(12) United States Patent
Cuddihy

(10) Patent No.: US 8,460,220 B2
(45) Date of Patent: Jun. 11, 2013

(54) SYSTEM AND METHOD FOR MONITORING THE GAIT CHARACTERISTICS OF A GROUP OF INDIVIDUALS

(75) Inventor: Paul Edward Cuddihy, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 417 days.

(21) Appl. No.: 12/641,481

(22) Filed: Dec. 18, 2009

(65) Prior Publication Data
US 2011/0152726 A1  Jun. 23, 2011

(51) Int. Cl.
*A61B 5/00* (2006.01)

(52) U.S. Cl.
USPC ........................................................ 600/595

(58) Field of Classification Search
USPC .................................................. 600/587, 595
See application file for complete search history.

(56) References Cited

U.S. PATENT DOCUMENTS

| | | | |
|---|---|---|---|
| 7,535,368 B2 * | 5/2009 | Graichen et al. ........... | 340/573.4 |
| 2006/0084847 A1 | 4/2006 | Reed et al. | |
| 2007/0069021 A1 | 3/2007 | Elrod et al. | |
| 2007/0276270 A1 | 11/2007 | Tran | |
| 2008/0146968 A1 | 6/2008 | Hanawaka et al. | |
| 2008/0186189 A1 | 8/2008 | Azzaro et al. | |
| 2008/0292151 A1 * | 11/2008 | Kurtz et al. ................... | 382/128 |
| 2009/0131836 A1 * | 5/2009 | Enohara et al. ............. | 600/595 |
| 2009/0254004 A1 | 10/2009 | Graichen et al. | |
| 2009/0257625 A1 | 10/2009 | Liu et al. | |

FOREIGN PATENT DOCUMENTS

| | | |
|---|---|---|
| WO | 2007081629 A2 | 7/2007 |
| WO | WO 2007081629 A2 * | 7/2007 |
| WO | 2009045235 A2 | 4/2009 |
| WO | 2010096907 A1 | 9/2010 |

OTHER PUBLICATIONS

Search Report from corresponding GB Application No. GB1021164.7 mailed on Apr. 14, 2011.

* cited by examiner

*Primary Examiner* — Max Hidenburg
(74) *Attorney, Agent, or Firm* — Marie-Claire B. Maple

(57) ABSTRACT

A system is provided for monitoring gait characteristics of a group of enrollees in a monitoring region of a public area. The system includes an identifying device to enroll the group of enrollees into the system by measuring identifying information. The system further includes a gait monitoring device to measure a sample gait characteristic during an enrollment phase, and to measure a gait characteristic of each enrollee subsequent to the enrollment phase. The system further includes an alerting device to receive an alert signal from the gait monitoring device, when the measured gait characteristic of a respective enrollee exceeds a safety threshold. The system further includes a display device to issue a trend report of the measured gait characteristic of a selectable enrollee for a selectable time period.

17 Claims, 4 Drawing Sheets

SYSTEM AND METHOD FOR MONITORING THE GAIT CHARACTERISTICS OF A GROUP OF INDIVIDUALS

BACKGROUND OF THE INVENTION

Gait characteristics are well-known and are measured to determine various aspects of how an individual walks, such as velocity, stride length, cadence, stride variability, for example. Although gait characteristics have been measured and monitored, to determine or predict the onset of one or more physical complications, the conventional use of measuring and monitoring gait characteristics has several drawbacks.

Conventional gait monitoring techniques are conducted by a qualified medical practitioner of a patient/resident in a medical center or treatment facility. However, based on resource and/or cost constraints, these gait monitoring techniques may only be conducted for specific circumstances, such as on a yearly or quarterly basis, or upon the determination of a health or safety event with the patient/resident, such as the occurrence of a fall, for example.

It would be advantageous to provide a system which addresses the shortcomings of the conventional gait monitoring techniques, to alleviate the resource and/or cost constraints, such that the gait monitoring may be conducted without the occurrence of such specific circumstances.

BRIEF DESCRIPTION OF THE INVENTION

In one embodiment of the present invention, a system is provided for monitoring gait characteristics of a group of enrollees in a monitoring region of a public area. The system includes an identifying device to acquire identifying information of each enrollee during an enrollment phase and to acquire identifying information of an individual having entered the monitoring region during a monitoring phase subsequent to the enrollment phase. Additionally, the system includes a processor to compare the acquired identifying information of the individual with the acquired identifying information of each enrollee during the enrollment phase, to determine if the individual is an enrollee. Additionally, the system includes a gait monitoring device to measure a sample gait characteristic of each enrollee during the enrollment phase. The gait monitoring device is also used to measure a gait characteristic of each enrollee during the monitoring phase, after the processor has determined that the individual is an enrollee. The processor also compares the measured gait characteristic of the enrollee with a previously-measured gait characteristic and/or the sample gait characteristic, to determine if the measured gait characteristic exceeds a safety threshold.

In another embodiment of the present invention, a system is provided for monitoring gait characteristics of a group of enrollees. The system includes an identifying device positioned in the monitoring region of the public area. The identifying device captures facial recognition data of an individual having entered the monitoring region of the public area. The system further includes a processor to compare the captured facial recognition data with a predetermined set of facial recognition data for the group of enrollees, to determine if the individual is an enrollee. The system further includes a gait monitoring device positioned in the monitoring area of the public area, to measure a gait characteristic of the enrollee, after the processor has determined that the individual is an enrollee. Additionally, the processor compares the measured gait characteristic with a previously-measured gait characteristic and/or a predetermined set of sample gait characteristic for each enrollee, to determine if the measured gait characteristic exceeds a safety threshold.

In another embodiment of the present invention, a method is provided for monitoring gait characteristics of a group of enrollees in a monitoring region of a public area. The method includes enrolling the group of enrollees, including measuring identifying information of each enrollee during an enrollment phase and measuring a sample gait characteristic of each enrollee during the enrollment phase. The method further includes monitoring the group of enrollees, including measuring a gait characteristic of each enrollee having entered the monitoring region of the public area. The method further includes alerting that the measured gait characteristic of a respective enrollee has exceeded a safety threshold. The method further includes displaying a trend report of the measured gait characteristic of a selectable enrollee for a selectable time period.

DETAILED DESCRIPTION

Figure 1:
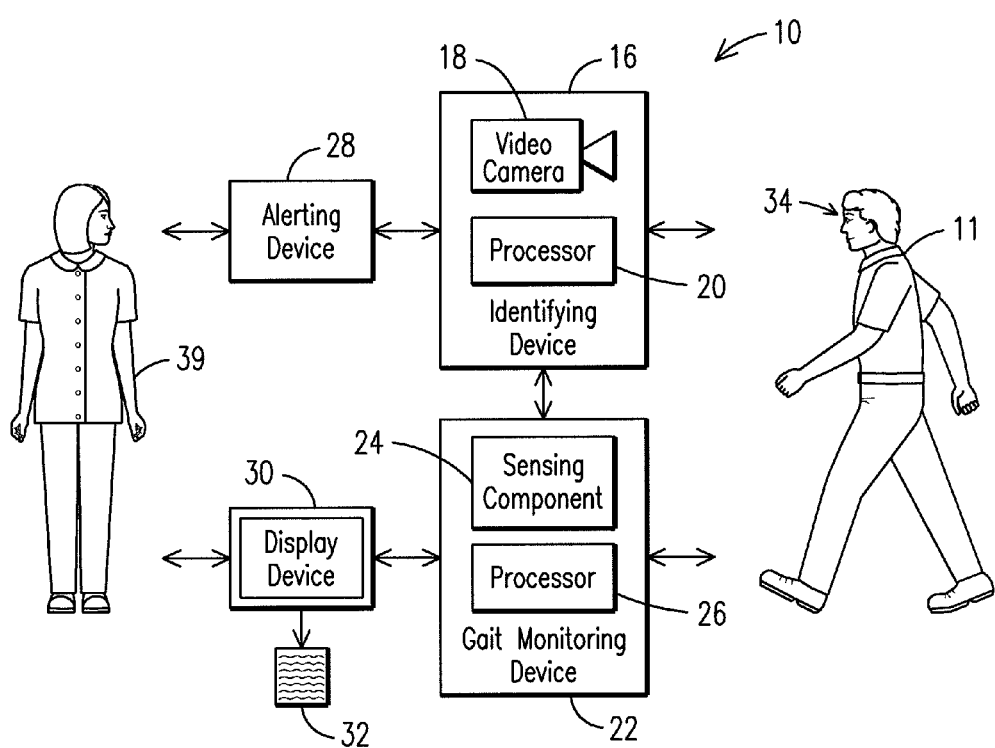
FIG. 1 is a schematic diagram of an exemplary embodiment of a system for monitoring gait characteristics of a group of enrollees in a monitoring region of a public area in accordance with the present invention.

As discussed above, the conventional gait monitoring techniques are performed by a qualified medical practitioner. Recently, conventional gait monitoring techniques have attempted to increase the frequency of the monitoring rate for each patient/resident, within the patient/resident's living area. However, this arrangement introduces various legal privacy issues and fails to address the cost constraints of the gait monitoring systems, in terms of the ratio of eligible patients/residents to each gait monitoring system. The inventor of the present application has devised a system which moves the gait monitoring system from the living area of the patient/resident into a common public area, so to address the legal privacy issues and the cost constraint issue, as the ratio of eligible patients/residents who may be monitored by the gait monitoring system in the common public area is much greater than in the living area of each patient/resident.

The exemplary embodiments of the present invention involve the use of gait characteristic monitoring systems, which are generally used to monitor and track a gait characteristic of an individual, in order to determine whether the gait characteristic is indicative of future health complications.

Such gait characteristics include but are not limited to velocity, stride length, cadence, phase information, stride variability, among others. This gait characteristic monitoring technology is disclosed in U.S. patent application Ser. No. 11/671,770 filed on Feb. 6, 2007, which is assigned to the assignee of the present application, and incorporated by reference herein. Thus, throughout the present application, when a reference is made to systems or technologies for monitoring and/or tracking "gait characteristics," such a reference is implicit to this incorporated disclosure information. As discussed in the incorporated disclosure information, various technologies are utilized in monitoring and/or tracking the gait characteristics of an individual, including but not limited to video, lidar, radar, IR (infra-red) and smart floors.

Smart floor technology involves the use of sensors on or within a floor surface which measure one or more gait characteristics (as discussed above), as the person walks over the smart floor. As oppose to the above-discussed technology, which measures/monitors the gait characteristic information with radiation sensors as they walk through a measurement area, the smart floor technology measures the gait characteristics using the sensors on or within the floor surface. The smart floor technology is disclosed in U.S. patent application Ser. No. 11/236,681 filed on Sep. 27, 2005, and is incorporated by reference herein. Throughout the discussion of the embodiments of the present invention, when a reference is made to "smart floor" technology, such a reference is implicit to this incorporated disclosure information.

The exemplary embodiments of the present invention frequently discuss acquiring identifying information of a person, such as an image of the person's face, and storing the image in a memory, in order to make a future determination if that same person enters a monitoring area. Facial recognition technology has been developed which accomplishes this objective, and is disclosed in U.S. patent application Ser. No. 12/100,620 filed on Apr. 10, 2008, which is assigned to the assignee of the present application. Accordingly, when a reference is made to acquiring a facial image of a person, storing the facial image and comparing a subsequent facial image with the stored facial images, to determine if the subsequent facial image is in the stored facial image database, such a reference is implicit to the above-referenced disclosure information.

Figure 2:
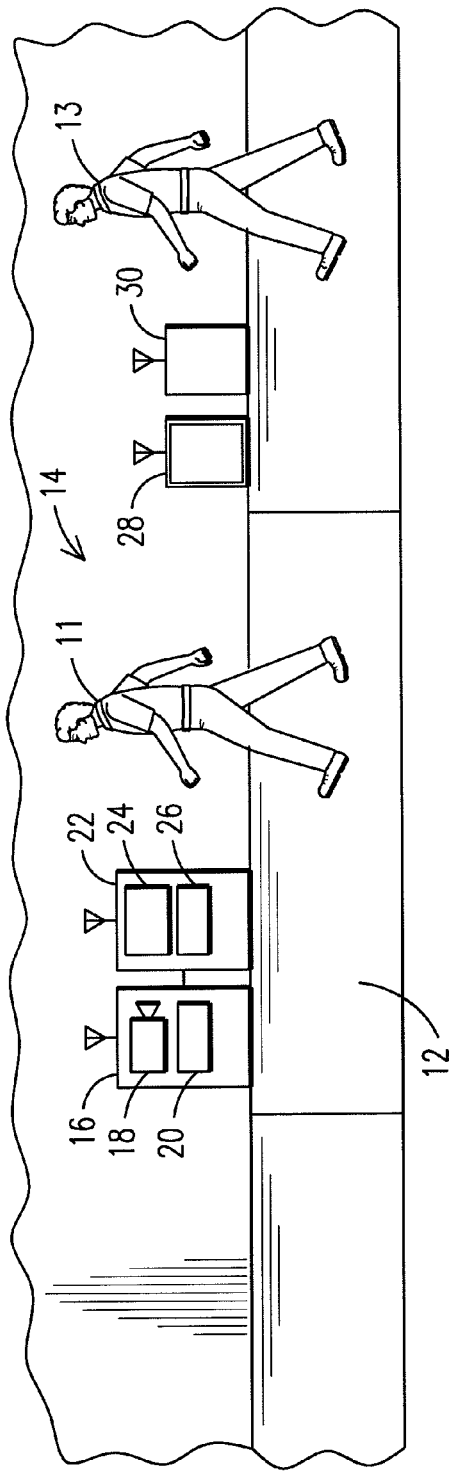
FIG. 2 is a perspective view of an exemplary embodiment of a system for monitoring gait characteristics of a first enrollee in a monitoring region of a public area in accordance with the present invention.
Figure 3:
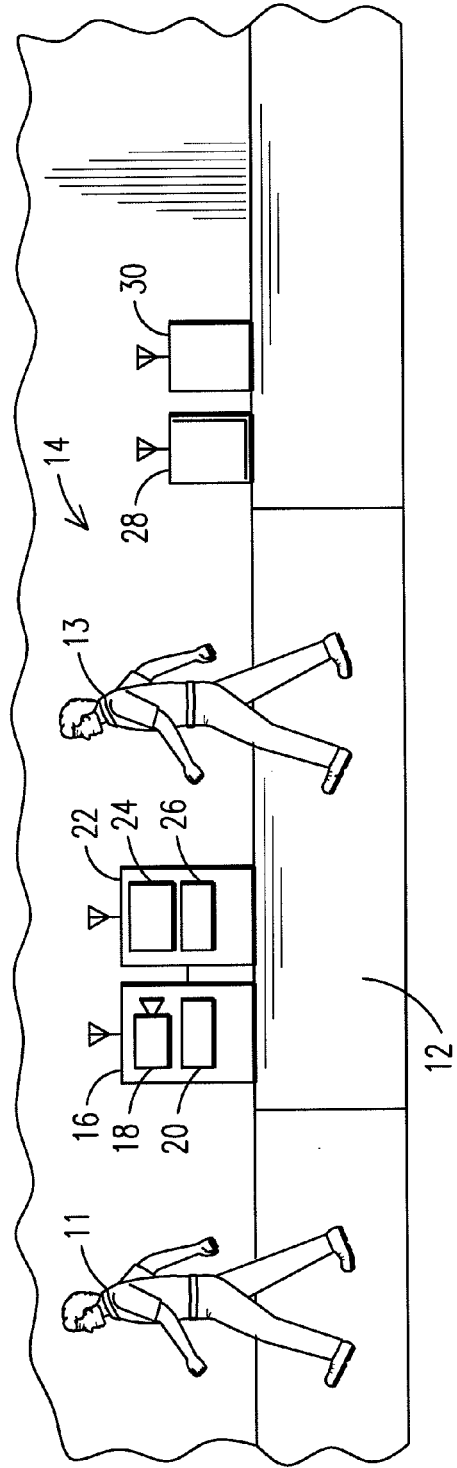
FIG. 3 is a perspective view of an exemplary embodiment of the system illustrated in FIG. 2, for monitoring gait characteristics of a second enrollee who entered the monitoring region after the first enrollee exited the monitoring region.

FIGS. 1-3 illustrates an exemplary embodiment of a system 10 for monitoring one or more gait characteristic(s) of a group of enrollees 11,13 in a monitoring region 12 of a public area 14. In an exemplary embodiment, the monitoring region 12 may be within a hallway of a medical facility, such as a senior assisted-living facility, through which one or more residents routinely pass through on a regular basis, to walk to a dining area of the facility, for example. However, the embodiments of the present invention are not limited to being utilized in any particular type of public area. For purposes of this disclosure, a "public area" may refer to any area in which an individual has a reduced expectation of privacy, in accordance with federal and state law and/or an area in which an individual is free to enter. For example, a sidewalk, hotel lobby or hallway within a medical facility (open to the public) would constitute such a public area, but not a room within the medical facility in which a resident sleeps.

As illustrated in FIG. 1, the system 10 includes an identifying device 16 which is used to enroll the enrollee 11 into the system 10, and to subsequently confirm the identity of enrollees after enrollment. The identifying device 16 captures identifying information of each enrollee 11 during an enrollment phase, such as a facial image of the enrollee 11, for example. The identifying device 16 includes a video camera 18 and a processor 20. However, the identifying device is not limited to video technology, and may use alternate technology such as RFID (radio frequency identification) to capture identifying information of the enrollee. During the enrollment phase, the enrollee 11 is prompted to position their face 34 in a field of view of the video camera 18, so that an image of the face 34, and any other information needed by the training/enrollment routines, is captured by the video camera 18 as the identifying information. After the video camera 18 has captured an image of the face 34 of the enrollee 11, the identifying information is stored in a memory of the processor 20, for each respective enrollee. However, the embodiment of the present invention is not limited to including the enrollment phase as described above, and a predetermined set of identifying information of enrollees may be input into the processor 20, thereby eliminating the need for the enrollment phase as described above, and instead utilizing an enrollment phase in which predetermined identifying information of the enrollees is obtained. For example, a predetermined set of identifying information of enrollees may be stored on a removable flash drive which may be read by the processor 20, to download this predetermined set of data.

As illustrated in FIG. 1, the system 10 further includes a gait monitoring device 22 to measure a sample gait characteristic of each enrollee 11 during the enrollment phase, and to subsequently measure a gait characteristic of each enrollee, upon entering the monitoring area 12 of the public area 14. The gait monitoring device 22 includes a sensing component 24 and a processor 26, where the sensing component 24 detects a gait characteristic of an individual who enters the monitoring region 12. In an exemplary embodiment, the sensing component 24 utilizes technology from, but not limited to, LIDAR, video, radar, active IR and smart floor technology, for example. During the enrollment phase, either prior to or subsequent to the capture of the facial image of the enrollee 11 by the video camera 18, the enrollee 11 is prompted to move within the monitoring region 12, such that the sensing component 24 measures the sample gait characteristic. After the sample gait characteristic is measured for each enrollee, the sample gait characteristic is stored within a memory of the processor 26, for each respective enrollee. Although the sample gait characteristic is discussed above as being measured during the enrollment phase for each enrollee, the enrollment phase need not include a measurement of the sample gait characteristic, but instead may just involve obtaining the identifying information of each enrollee, and measuring gait characteristic data when each enrollee enters the monitoring region 12 subsequent to the enrollment phase. Thus, upon enrollment of the enrollee 11, the processor 20 of the identifying device 16 has stored the image of the face 34 of the enrollee 11, while the processor 26 of the gait monitoring device 22 has stored the sample gait characteristic of the enrollee 11. As illustrated in FIGS. 2-3, the identifying device 16 and gait monitoring device 22 are coupled together, either by a hard-wire connection or a wireless connection, such that the enrollment data of the enrollee 11 is shared between the devices 16,22.

In the illustrated embodiments of FIGS. 2-3, upon entering the monitoring region 12 of the public area 14, the first enrollee 11 can enroll in the system 10 by providing the facial image to the video camera 18, and the sample gait characteristic to the sensing component 24, as discussed above. In an exemplary embodiment, either or both of the identifying device 16 and gait monitoring device 22 may request the consent of the first enrollee 11 to be enrolled in the system 10, in order to avoid privacy issues. In an exemplary embodiment, the public area 14 is chosen such that it is already provided with existing video cameras or surveillance (not shown) and thus the addition of the video camera 18 and sensing component 24 is not presumed to raise a privacy issue. However, the embodiments of the present invention are not limited to being utilized within an area which has existing video cameras or surveillance. After the first enrollee 11 has enrolled in the system 10, either by receiving visual confirmation on a display (not shown) on one of the identifying device 16 and/or gait monitoring device 22, the first enrollee 11 moves out of the monitoring region 12 (FIG. 3) and a second enrollee 13 enters the monitoring region 12. The second enrollee 13 may now enroll in the system 10, if they so choose, using the same process as the first enrollee 11. As previously discussed, in an exemplary embodiment, the monitoring region 12 is within a public area 14, such as a hallway of a senior assisted-living facility, through which residents may routinely walk, such as to a dining area, for example, and thus the first enrollee 11 is presumed to continue on a pre-existing path through the monitoring region 12 and public area 14.

Upon enrollment of the first and second enrollee 11,13, if either of the enrollees 11,13 re-enter the monitoring region 12 of the public area 14, the video camera 18 will confirm their identity, using a facial recognition technique. For example, the video camera 18 will capture a facial image of an individual who enters the monitoring region 12, and compare it with each of the stored facial images of enrollees 11,13 in the memory of the processor 20. If the captured image matches the facial image of the first enrollee 11, for example, the identifying component 16 sends an activation signal to the gait monitoring device 22, to capture gait characteristic data of the first enrollee 11 as they walk through the monitoring region 12, with the sensing component 24. If, however, the captured image of the individual does not match the facial image of any enrollee in the memory of the processor 20, neither the identifying component 16 nor the gait monitoring device 22 take any action regarding the individual, as they pass through the monitoring region 12. After the sensing component 24 has captured gait characteristic data of the first enrollee 11 as they walk through the monitoring region 12, the processor 26 compares this captured gait characteristic data with previously-captured gait characteristic data and/or the sample gait characteristic data of the first enrollee 11, already stored in the memory of the processor 26. Based on this comparison, the processor 26 determines whether the captured gait characteristic data exceeds a safety threshold, and if so, transmits an alert signal to an alerting device 28. In an exemplary embodiment, the safety threshold may apply both to an absolute gait characteristic measured by the gait monitoring device 22, as well as a trend of collected gait characteristic data captured over a period of time. For example, the safety threshold may be individualized for each enrollee, and based on the enrollee's most recent captured gait characteristic by the gait monitoring device 22, in which case the processor 26 compares the captured gait characteristic with the most-recent captured gait characteristic, such as the day before, in order to determine whether to transmit an alert signal. In performing this comparison, the processor 26 may be programmed to identify outliers within the captured gait characteristic which are not attributable to the enrollee 11 walking through the monitoring region 12, and to eliminate this outlier from the comparison, such as an outlier being indicative of the enrollee 11 stopping in the monitoring region 12 to talk to another individual or drink from a water fountain, for example.

As illustrated in FIG. 1, a medical staff member 39 may respond to this alert signal, and take the necessary measures to ensure that the doctor and/or medical training staff of the enrollee are notified that the gait characteristic of the first enrollee 11 has exceeded a safety threshold. In an exemplary embodiment, in which the public area 12 is in a senior assisted-living facility, the system 10 and the alert signal to the alerting device 28 may be indicative that the enrollee has a risk of falling. The embodiments of the present invention are not limited to being used within a medical facility, and thus any individual including the enrollee themselves could respond to the alert signal, not necessarily a medical staff member.

As described above, after the sensing component 24 captures gait characteristic data of the first enrollee 11 as they walk through the monitoring region 12, this captured gait characteristic data is transmitted to a display device 30 where it is stored, for the first enrollee 11. As illustrated in FIG. 1, as with the alerting device 28, the medical staff member 39 can interact with the display device 30, where the staff member 39 may select an enrollee and a period of time, and the display device 30 outputs a trend report 32 of the measured gait characteristics of the selected enrollee over the selected period of time. Such trend reports 32 may be displayed on a display (not shown) of the display device 30, or output in hard-copy format. The trend reports 32 may be shown to the enrollee's doctors and medical staff, in addition to the family of the enrollee, as tangible evidence of a need for a modification in care, for example.

Figure 4:
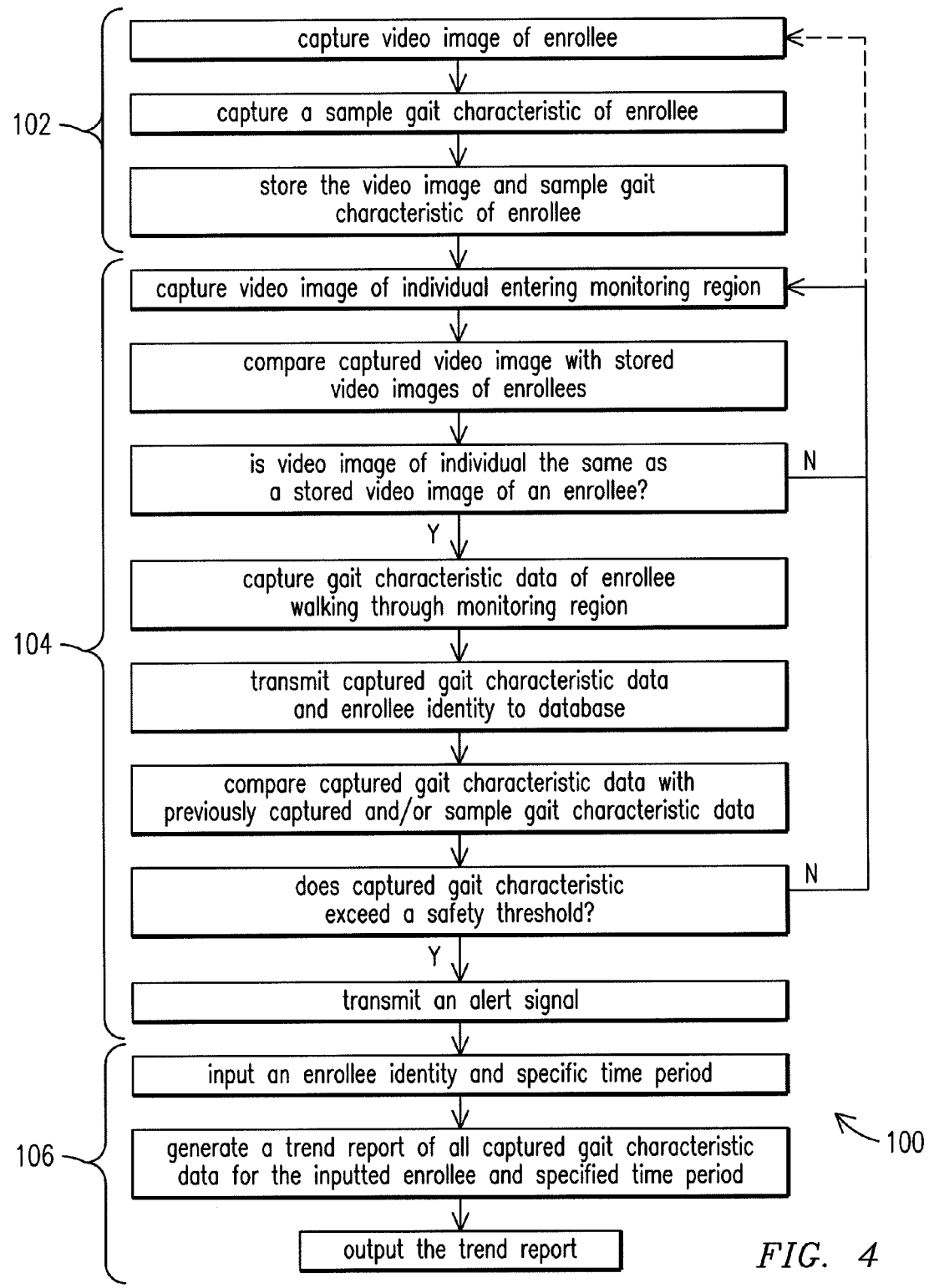
FIG. 4 is a flowchart depicting an exemplary embodiment of a method for of an exemplary embodiment of a system for monitoring gait characteristics of a group of enrollees in a monitoring region of a public area in accordance with the present invention.

FIG. 4 illustrates a flowchart depicting a method 100 for enacting a process embodying the system 10 described above in the embodiments of FIGS. 1-3. The method 100 involves an enrollment phase 102, a monitoring/alerting phase 104 and a displaying/trending phase 106. As previously discussed, during the enrollment phase 102, the enrollee 11 enters the monitoring region 12, after which the video camera 18 captures a video image of the face of the enrollee 11, the sensing component 24 captures a sample gait characteristic of the enrollee 11, and both of the video image and sample gait characteristic are stored. The enrollment phase 102 is continued, as long as individuals are in the monitoring region 12 and desire to be enrolled. As previously discussed in the above embodiments, the enrollees may be requested to provide their consent to be enrolled.

After each enrollee has undergone the enrollment phase 102, the method 100 passes to the monitoring/alerting 104 phase, which commences when an individual walks into the monitoring region 12. The video camera 18 captures an image of the face of the individual, and the processor 20 compares the captured video image with the stored video images of the enrollees. A determination is then made by the processor 20 as to whether the captured video image of the individual's face matches one of the stored video images of the enrollees. If no such match is found, the method 100 returns to awaiting the entrance of another individual into the monitoring region 12, or to the enrollment phase 102, in the event that a new enrollee approaches the video camera 18. On the other hand, if such a match is found, the monitoring/alerting phase 104 continues to the sensing component 24 capturing gait characteristic data of the individual/enrollee as they walk through the monitoring region 12. The gait monitoring device 22 transmits this captured gait characteristic data, along with the enrollee information, to the display device 30, which is subsequently stored in a memory (not shown) of the display device, for purposes of production of a trend report 32, as discussed below. The processor 26 of the gait monitoring device 22 then compares the captured gait monitoring data with the previously-captured gait monitoring data and/or the sample gait monitoring data acquired during enrollment. Based on this comparison, the processor 26 makes a determination as to whether the captured gait monitoring data exceeds a safety threshold. If the captured gait monitoring data does not exceed such a safety threshold, the method 100 returns to awaiting for a subsequent individual to enter the monitoring region 12, or to the enrollment phase 102, in the event that a new enrollee approaches the video camera 18. However, if the captured gait monitoring data does exceed such a safety requirement, an alert signal is transmitted from the gait monitoring device 22 to the alerting device 28, such that a medical staff member 39 (or other appropriate party) is informed of the variation in the gait characteristic of the enrollee.

Subsequent to the issuance of the alert signal to the alerting device 28, the method 100 may proceed to the displaying/trending 106 phase, in which the medical staff member 39 (or other appropriate party) approaches the display device 30, and inputs the identity of the enrollee referenced in the alert signal, as well as a time period over which the staff member 39 desires to see the previously captured gait monitoring data of the enrollee. The display device 30, in which the previously captured gait characteristic data is stored for the enrollee, generates a trend report 32 of the specified enrollee for the previously specified time period, and outputs this trend report 32. Based on the trend report, the staff member 39 may inform the physician or treating staff of the enrollee and/or the family of the enrollee, in order to modify any necessary rehab or treatment of the enrollee. Although the use of the display device 30 is discussed herein as a staff member 39 responding to an alert signal, a staff member 39 (or any appropriate party) may use the display device 30 at any time, with or without the issuance of an alert signal.

Figure 5:
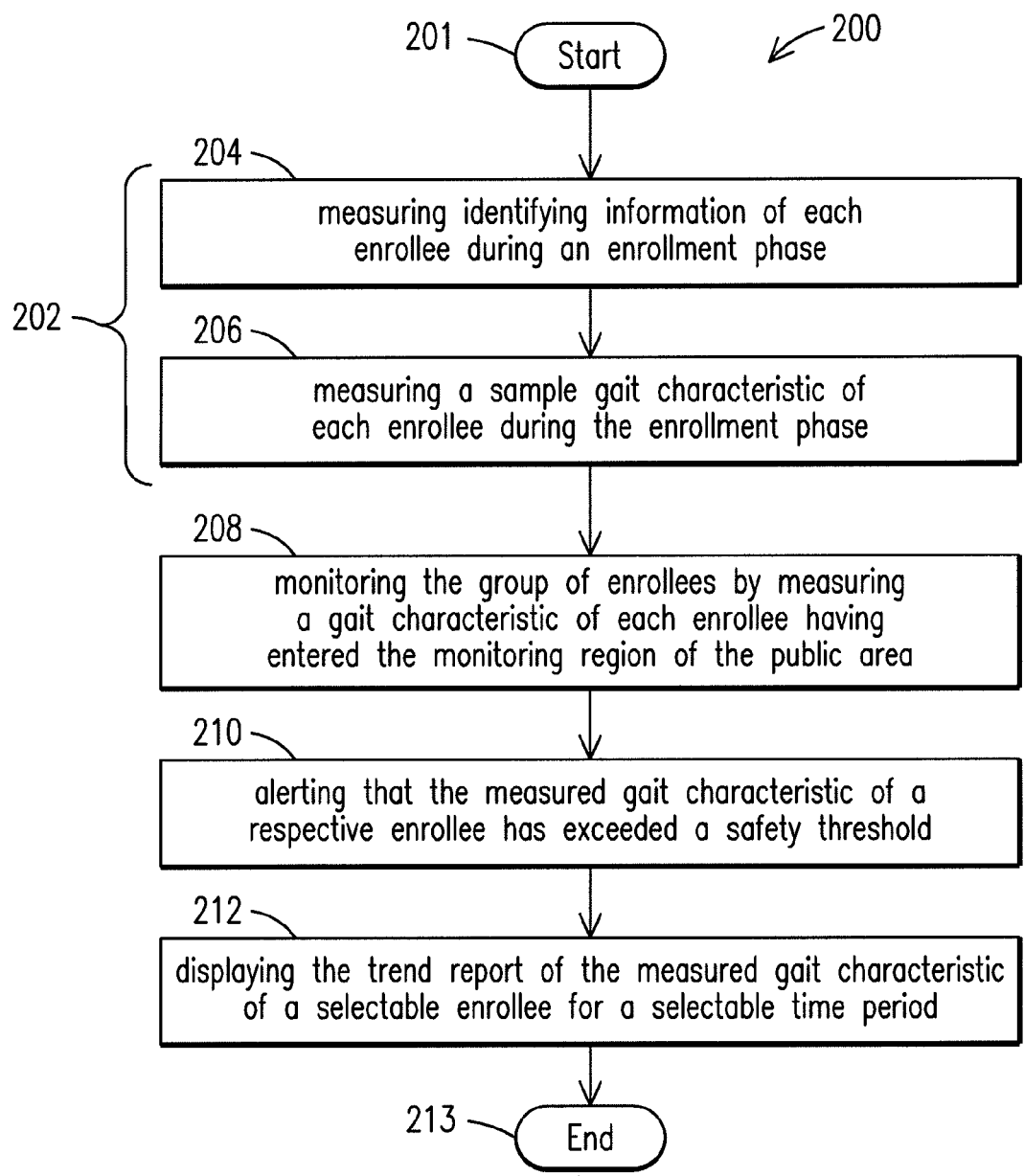
FIG. 5 is a flowchart depicting an exemplary embodiment of a method for of an exemplary embodiment of a system for monitoring gait characteristics of a group of enrollees in a monitoring region of a public area in accordance with the present invention.

FIG. 5 illustrates a flowchart depicting a method 200 for monitoring gait characteristics of the group of enrollees 11,13 in the monitoring region 12 of the public area 14. The method 200 begins at 201 by enrolling 202 the group of enrollees 11,13 by measuring 204 identifying information of each enrollee 11,13 during an enrollment phase and measuring 206 a sample gait characteristic of each enrollee 11,13 during the enrollment phase. Additionally, the method 200 includes monitoring 208 the group of enrollees 11,13 by measuring a gait characteristic of each enrollee 11,13 having entered the monitoring region 12 of the public area 14. The method 200 further includes alerting 210 that the measured gait characteristic of a respective enrollee 11,13 has exceeded a safety threshold. The method 200 further includes displaying 212 the trend report 32 of the measured gait characteristic of a selectable enrollee for a selectable time period, before ending at 213. The method 200 does not require that both of the alerting 210 and display 212 steps are performed, nor that either of these steps are performed.

This written description uses examples to disclose embodiments of the invention, including the best mode, and also to enable any person skilled in the art to make and use the embodiments of the invention. The patentable scope of the embodiments of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for monitoring gait characteristics of one or more enrollees in a monitoring region of a public area, said system comprising:

an identifying device comprising a video camera positioned in the monitoring region of the public area, wherein the identifying device is configured to:
    automatically prompt a potential enrollee having entered the monitoring region of the public area to provide consent for monitoring the enrollee in the monitoring region, and
    enroll the enrollee on receiving the enrollee's consent, said enrolling including automatically prompting the enrollee to move to a designated location in the monitoring region of the public area to acquire identifying information of the enrollee during an enrollment phase and automatically prompting the enrollee to move in monitoring region within a field of view of the video camera to measure a sample gait characteristic of the enrollee during the enrollment phase; and
    acquire identifying information of one or more individuals having entered the monitoring region during a monitoring phase subsequent to the enrollment phase;
a processor configured to identify the enrollee from the one or more individuals in the monitoring region by comparing the acquired identifying information of the one or more individuals in the monitoring region with the acquired identifying information of the enrollee during the enrollment phase to determine if one of the individuals is the enrollee; and
a gait monitoring device configured to measure the sample gait characteristic of the enrollee during the enrollment phase; said gait monitoring device being further configured to measure a gait characteristic of the enrollee during the monitoring phase, if the processor identifies that one of the individuals is the enrollee;
wherein said processor is further configured to compare the measured gait characteristic of the enrollee with at least one of a previously-measured gait characteristic and the sample gait characteristic of the enrollee, to determine if the measured gait characteristic exceeds a safety threshold.

2. The system of claim 1, further comprising:
an alerting device configured to receive an alert signal from said gait monitoring device, said alert signal based on the measured gait characteristic of the enrollee having exceeded the safety threshold; and
a display device configured to receive said measured gait characteristic data and the enrollee's identifying information of said measured gait characteristic from said gait monitoring device; said display device further configured to issue a trend report of the measured gait characteristic of a selectable enrollee for a selectable time period.

3. The system of claim 2, wherein the identifying device includes a video camera; wherein during said enrollment phase, said enrollee is prompted to position the enrollee's face in a field of view of the video camera to capture an image of the face as said identifying information; wherein said identifying information is stored in a memory of said processor.

4. The system of claim 2, wherein said gait monitoring device comprises a sensing component, said sensing component being configured to detect the gait characteristic of the one or more individuals, said sensing component configured to detect said sample gait characteristic of the enrollee during the enrolment phase; wherein said sample gait characteristic for each respective enrollee is stored within a memory of said processor.

5. The system of claim 4, wherein upon an individual having entered the monitoring area, said video camera is configured to capture an image of the individual's face, and is configured to compare the captured face image with stored face images of enrollees in the memory of the processor; wherein said identifying device is configured to transmit an activate signal to the gait monitoring device if the captured face image corresponds to a stored face image of the enrollee, such that upon receiving the activate signal, said gait monitoring device is configured to measure and store a gait characteristic of the individual moving through the monitoring area, and transmit the measured gait characteristic and identifying information to the display device, and transmit an alert signal to the alert device, in the event that the measured gait characteristic exceeds the safety threshold.

6. The system of claim 5, wherein said identifying device is configured to take no action if the captured face image does not correspond to a stored face image of the enrollee, and thus the gait monitoring device does not measure the gait characteristic of the individual moving through the monitoring area.

7. The system of claim 4, wherein said sensing component incorporates at least one of LIDAR, video, radar, active infrared, and smart floor technology.

8. The system of claim 2, wherein the display device is configured to output the trend report of the measured gait characteristics for the enrollee for a selectable time period based on the received alert signal at the alerting device, including a measured gait characteristic exceeding the safety threshold and the enrollee's identifying information to diagnose any future complications of the enrollee.

9. The system of claim 1, wherein said monitoring area of the public area is a hallway where said enrollees frequently pass through on a routine basis.

10. The system of claim 1, wherein said monitoring area of the public area is a hallway in a senior assisted-living facility; and wherein said alert signal and trend reports are utilised to forecast an oncoming risk of falling.

11. The system of claim 1, wherein an existing video camera is provided in the public area, such that the identifying device is a redundant video camera in the public area.

12. A system for monitoring gait characteristics of one or more enrollees, said system comprising:
an identifying device positioned in a monitoring region of a public area, said identifying device configured to:
automatically prompt a potential enrollee having entered the monitoring region of the public area to provide consent for monitoring the enrollee in the monitoring region,
enroll the enrollee on receiving the enrollee's consent, said enrolling including automatically prompting the enrollee to move to a designated location in the monitoring region of the public area to capture corresponding facial recognition data and automatically prompting the enrollee to move within the monitoring region for measuring a sample gait characteristic of the enrollee;
a processor configured to identify the enrollee from one or more individuals having entered the monitoring region by comparing the captured facial recognition data with a predetermined set of facial recognition data for the one or more enrollees to determine if one of the individuals is the enrollee;
a gait monitoring device positioned in the monitoring area of the public area, said gait monitoring area configured to measure the sample gait characteristic of the enrollee, if the processor determines that one of the individuals is the enrollee;
said processor being further configured to compare the sample gait characteristic with at least one of a previously-measured gait characteristic and a predetermined set of sample gait characteristic for the enrollee to determine if the measured gait characteristic exceeds a safety threshold.

13. The system of claim 12, further comprising:
an alerting device positioned in the monitoring area of the public area, said alerting device configured to receive an alert signal from said gait monitoring device, said alert signal being indicative of the measured gait characteristic of the enrollee having exceeded the safety threshold; and
a display device positioned in the monitoring area of the public area, said display device configured to receive and store said measured gait characteristic data for the enrollee, said display device further configured to issue a trend report of the measured gait characteristic of a selectable enrollee for a selectable time period.

14. The system of claim 12, wherein said monitoring area in the public area is a hallway of a medical treatment facility, through which the enrollees pass through on a routine basis.

15. The system of claim 14, wherein said monitoring area in the public area is a hallway in a senior assisted-living facility, through which the enrollees pass through on a routine basis, and wherein said alert signal and trend report is utilised to reduce a future likelihood of falling of the enrollees within the senior assisted living facility.

16. The system of claim 12, wherein said identifying device includes a video camera and a processor; wherein during an enrollment phase, said predetermined set of facial recognition data for the one or more enrollees is captured by the video camera by prompting each enrollee to position the enrollee's face in a field of view of the video camera to capture the facial recognition data; wherein said facial recognition data of each enrollee is stored in a memory of said processor.

17. A method for monitoring gait characteristics of one or more enrollees in a monitoring region of a public area, said method comprising:
automatically prompting a potential enrollee having entered the monitoring region of the public area to provide consent for monitoring of gait characteristics in the monitoring region;
enrolling the enrollee on receiving the enrollee's consent, said enrolling including automatically prompting the enrollee to move to a designated location in the monitoring region of the public area for measuring identifying information of the enrollee during an enrollment phase and automatically prompting the enrollee to move within the monitoring region for measuring a sample gait characteristic of the enrollee during the enrollment phase;
monitoring one or more individuals having entered the monitoring region to acquire corresponding identifying information;
identifying the enrollee from the one or more individuals by comparing the identifying information of the enrollee with the identifying information of the one or more individuals in the monitoring region with the acquired identifying information of the enrollee during the enrollment phase;
measuring a gait characteristic of the enrollee upon identifying that one of the individuals is the enrollee;
comparing the measured gait characteristic of the enrollee with at least one of a previously-measured gait characteristic and the sample gait characteristic of the enrollee, to determine if the measured gait characteristic exceeds a safety threshold and alerting if the measured gait characteristic of the enrollee has exceeded a safety threshold; and displaying a trend report of the measured gait characteristic of the enrollee for a selectable time period, wherein displaying a trend report comprises selecting the enrollee from the one or more enrollees.

\* \* \* \* \*